United States Patent [19]

Budinger

[11] Patent Number: 4,970,897

[45] Date of Patent: Nov. 20, 1990

[54] METHOD AND APPARATUS FOR DETERMINATION AND DISPLAY OF GAS CONSUMPTION TIME

[76] Inventor: William D. Budinger, 19 Southridge Dr., Kennett Square, Pa. 19348

[21] Appl. No.: 448,026

[22] Filed: Dec. 8, 1989

Related U.S. Application Data

[60] Continuation-in-part of Ser. No. 308,509, Feb. 9, 1989, Pat. No. 4,926,703, which is a division of Ser. No. 169,651, Mar. 21, 1988, Pat. No. 4,876,903, which is a continuation-in-part of Ser. No. 142,370, Jan. 11, 1988, abandoned.

[51] Int. Cl.[5] .............................................. G06F 15/42
[52] U.S. Cl. ................................... 73/432.1; 73/865.1
[58] Field of Search ..................... 73/865.1, 714, 432.1; 364/418, 705, 413.3, 413.31; 340/700, 717; 128/205.23

[56] References Cited

U.S. PATENT DOCUMENTS

| | | | |
|---|---|---|---|
| 3,364,476 | 1/1968 | Kahn | 340/213 |
| 4,109,140 | 8/1978 | Etra | 235/92 MT |
| 4,586,136 | 4/1986 | Lewis | 364/418 |
| 4,658,358 | 4/1987 | Leach et al. | 364/418 |
| 4,736,348 | 4/1988 | Bednarczyk | 367/69 |
| 4,753,117 | 6/1988 | Osterhout et al. | 73/865.1 |
| 4,782,338 | 11/1988 | Barshinger | 340/754 |
| 4,809,550 | 3/1989 | Faulconer | 73/865.1 |

Primary Examiner—Robert Raevis
Attorney, Agent, or Firm—Panitch Schwarze Jacobs & Nadel

[57] ABSTRACT

A portable, battery powered apparatus is provided for determining and displaying the amount of time that a fixed supply of breathable gas can sustain a consumer who wishes to breathe the gas at one or more ambient pressures. The apparatus include a device for measuring the ambient pressure in the vicinity of the consumer at least once every ten second and for generating signals representative of the ambient pressure. A device is provided for measuring the pressure of the supply gas and for generating signals representative of the supply gas pressure. The apparatus preferably includes a programmed microprocessor which periodically receives a series of supply gas pressure measurement signals and periodically determines from the series of supply gas pressure measurement signals the average rate at which the supply gas was consumed (Consumption Rate) over a time at least five times as long as the average time between the supply gas pressure measurements. A normalized Consumption Rate is determined by normalizing each determined Consumption Rate to compensate for the ambient pressure on the consumer during the time period over which the Consumption Rate was determined. A normalized Consumption Time is determined by dividing a supply gas pressure measurement by the normalized Consumption Rate. A projected Consumption Time is determined for one or more ambient pressures of interest by adjusting the normalized Consumption Time to each ambient pressure of interest. A display is provided for receiving and displaying to the consumer one or more projected Consumption Times and one or more associated ambient pressures.

5 Claims, 1 Drawing Sheet

METHOD AND APPARATUS FOR DETERMINATION AND DISPLAY OF GAS CONSUMPTION TIME

CROSS-REFERENCE TO RELATED APPLICATIONS

This application is a continuation-in-part of U.S. patent application Ser. No. 308,509 filed Feb. 9, 1989 now U.S. Pat. No. 4,426,703, which is a divisional of U.S. patent application Ser. No. 169,651 filed Mar. 21, 1988, now U.S. Pat. No. 4,876,903, which is a continuation-in-part of U.S. patent application Ser. No. 142,370 filed Jan. 11, 1988, now abandoned.

FIELD OF THE INVENTION

This invention relates to systems for breathing a breathable gas from a pressurized fixed volume container such as SCUBA, medical and aircraft oxygen, and the like, and, in particular, relates to a portable, battery powered apparatus for the determination and display to a user of an accurate prediction of the amount of time that such a fixed volume container of gas will sustain the user, instantaneously adjusted for changes or potential changes in the user's ambient pressure.

BACKGROUND OF THE INVENTION

In the use of self-contained or supplemental breathing systems which draw from a fixed volume source, it is often desirable for the user to be able to predict how long the remaining air or gas supply will last. In SCUBA (Self-Contained Underwater Breathing Apparatus) diving, for example, it is particularly useful to know how long a diver may continue at the present task and still have enough air to make a safe ascent to the surface. For systems supplying oxygen to people in unpressurized aircraft, it is useful to know how long the supply of oxygen will last, particularly if the aircraft changes altitude.

Present practice makes use of pressure gauges to tell the user the remaining air or gas pressure and charts that list schedules showing how much time can be expected for a given tank volume and pressure. In SCUBA diving, for example, divers are trained to know that a typical 72 cubic foot tank pressurized to 2250 psi will last about one hour at a depth of 33 feet (10 meters). The diver also knows that that same amount of air will last only half as long at a depth of 99 feet (30 meters). Accurately estimating how much time remains with a given supply of air is difficult for a diver who is changing depths or an aviator who is changing altitudes.

The reason that endurance time varies with changes in depth or altitude is due to a combination of human physiology and Boyle's Laws of gases. A typical person tends to breathe volumetrically without regard to the ambient pressure. A typical person may breathe about one cubic foot of air per minute based upon an average respiration rate. This breath volume stays about the same whether the person is in an unpressurized airplane at 18,000 feet or in a pressurized diving bell 200 feet below the surface of the sea. However, the actual amount of gas represented by each breath at these two extremes is very different. According to Boyle's Law, the number of gas molecules in a given volume of gas is directly proportional to the absolute pressure (all other things being unchanged). At 18,000 feet, the absolute pressure is about one-half of an atmosphere (½ Bar). At a depth of 200 feet of sea water, the absolute pressure is about 7 atmospheres (7 Bars). This means that a person breathing 4 liter breaths at a depth of 200 feet of sea water is using about 14 times as much air per breath as a person at 18,000 feet. Thus, if the person is breathing from a fixed supply such as a tank, ambient pressure has a tremendous effect on how long the air within the tank will last. For example, a 72 cubic foot SCUBA tank will provide air for about 3 hours to an aviator at an altitude of 18,000 feet, but the same tank will provide air for only about 13 minutes to a diver 200 feet under the surface of the sea. Thus, all other things being equal, the pressure Consumption Rate for a person breathing from a fixed volume container is directly proportional to the absolute ambient pressure and the amount of time that a fixed supply of air within such a container will support a person's breathing is inversely proportional to the absolute ambient pressure.

The distinction between volumetric Consumption Rate and pressure Consumption Rate is essential to understanding of this invention. Pressure Consumption Rate is simply the rate at which the pressure of the gas in the fixed container is dropping as a result of consumption. Pressure Consumption Rate is easy to measure and is the basis for the calculations made by this invention. The relationship between pressure Consumption Rate (CRp) and volumetric Consumption Rate (CRv) can be expressed by the formula:

$$CRp = (CRv)(Pa)$$

Where:
Pa = ambient pressure

This equation will be accurate for any units provided that the same units are used throughout and all pressures are expressed in absolute.

In the following discussion, the term "air" is used for simplicity, but "air" should be taken to mean any breathable gas or mixture of breathable gases. Air supply levels and Consumption Rates are referred to in terms of pressure rather than volume or mass because pressure and pressure changes are easy to measure and work well for the present purpose. To illustrate the invention, the SCUBA model will be used, although the principles apply equally to any other situation in which gas is being breathed from a fixed volume container.

Estimating the amount of time a SCUBA diver's compressed air supply will last is exceedingly important. As might be expected, such estimates are very difficult to accurately make when the diver operates at many different depths. Further, the diver must have enough air left in his tank to make it to the surface safely.

The prior art has attempted to estimate or compute a gas Consumption Rate in various ways and to make projections of how long the remaining supply of air will last (Projected Consumption Time) at the computed gas Consumption Rate. The most common prior art method has been to measure the gradual reduction in gas supply pressure and then to calculate the remaining time by directly extrapolating that reduction rate over the remaining gas supply pressure. In addition to being slow to register response to changing Consumption Rate as a result of changing depths, the prior art approach is unable to quickly and accurately predict and display Projected Consumption Time for ambient pressures other than the pressure (depth) at which the diver is then located.

The prior art approach also must necessarily respond slowly to changes in the rate at which air is consumed. Otherwise, the prior art would be unduly influenced by changes in tank air pressure caused by events other than breathing. For example, a diver occasionally uses tank air for non-breathing purposes such as clearing a regulator, inflating a buoyancy compensator, or inflating a lift bag, all of which affect air consumption. In addition, short bursts of exertion or excitement by a diver can produce significant short term variations in air consumption. Thus, the calculation of Consumption Rate must be made over a fairly long term to avoid being unduly influenced by such atypical short term air usage and to provide a more accurate indication of true Consumption Rate. While such long term calculations are desirable for avoiding the effects of atypical air usage, genuine changes in the long term Consumption Rate (such as those caused by changing depth), are slow to be recognized.

The present invention overcomes the problems associated with the prior art approach and provides an accurate determination of the actual Consumption Rate by frequently averaging changes in the container air pressure (for example, every 15 seconds) over a relatively long period of time (for example, 3 minutes) based upon a series of tank pressure measurements over the averaging period. A Consumption Rate for the current ambient pressure is determined and a Projected Consumption Time at the current or some other ambient pressure is determined and displayed. The calculated Projected Consumption Time can then be adjusted instantaneously whenever the ambient pressure is changed.

SUMMARY OF THE INVENTION

Briefly stated, the present invention comprises an apparatus for determining and displaying the amount of time that a fixed supply of pressurized breathable gas can sustain a consumer breathing the gas at one or more ambient pressures. The apparatus comprises means for measuring the ambient pressure in the vicinity of the consumer at least once ever ten seconds and for generating signals representative of the ambient pressure. Means are provided for measuring the pressure of the supply gas and for generating signals representative of the supply gas pressure. Means are provided for receiving a series of two or more supply gas pressure measurement signals and for periodically determining, from the series of supply gas measurement signals, the average rate at which the supply gas was consumed (Consumption Rate) over a time interval which is at least five times as long as the average time interval between the ambient gas pressure measurements. A Projected Consumption Time is determined based on the determined Consumption Rate and the measured pressure of the supply gas. Means are provided for determining a Projected Consumption Time at one or more ambient pressures by normalizing at least one of the constituent measurements and subsequently converting the normalized result to a new ambient pressure of interest. Means may also be provided for receiving and displaying in a two-dimensional graphic form various Projected Consumption Times at associated ambient pressures.

BRIEF DESCRIPTION OF THE DRAWINGS

The foregoing summary, as well as the following detailed description of preferred embodiments of the invention will be better understood when read in conjunction with the appended drawings. For the purpose of illustrating the invention, there is shown in the drawings embodiments which are presently preferred. It is understood, however, that the invention is not limited to the precise arrangement and instrumentalities shown. In the drawings.

DETAILED DESCRIPTION OF THE INVENTION

Figure 1:
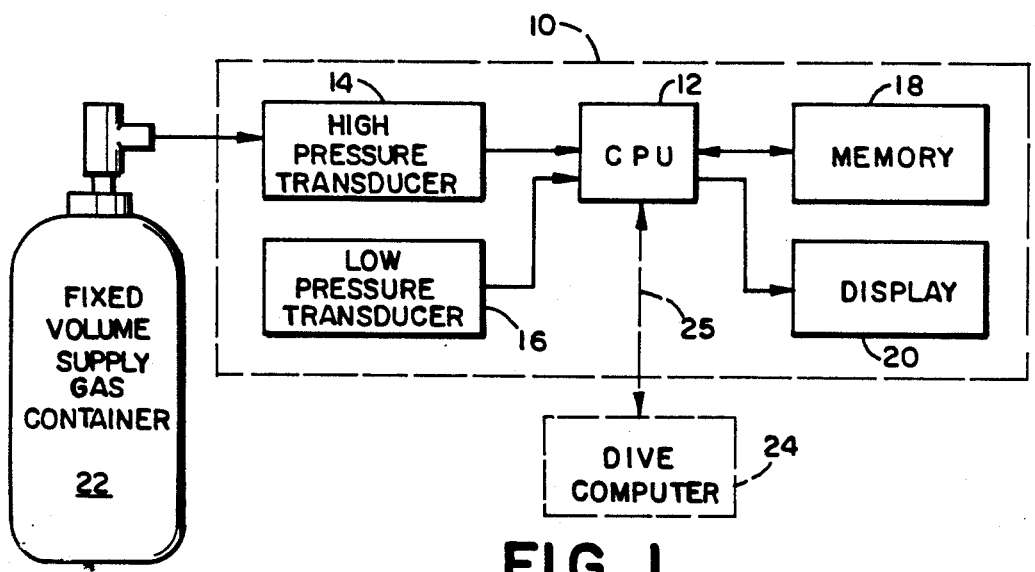
FIG. 1 depicts in block diagram form the basic components of the, preferred apparatus of the present invention.

FIG. 1 depicts diagrammatically the major components of a preferred embodiment of an apparatus 10 in accordance with the present invention. The apparatus 10 is portable and battery powered and includes a microprocessor-based CPU 12 or other form of electrical circuit capable of performing the necessary calculations and determinations described in detail below. A first, high pressure measuring transducer 14 is configured to measure the supply gas pressure in a fixed volume container 22 of breathable gas. A second, low pressure measuring transducer 16 senses or measures ambient pressure to determine the depth of the user of the apparatus 10. A display 20 is controlled by the CPU 12 and presents information to the user. The high pressure transducer 14 is a means for sensing or measuring the pressure of the supply gas within the container 22 and for generating electrical signals proportional to or representative of the supply gas pressure within the container 22, which are sent to the CPU 12. The low pressure transducer 16 is a means for sensing or measuring the current ambient pressure within the vicinity of the user of the apparatus 10 and for generating electrical signals proportional to or representative of the current ambient pressure, which are also sent to the CPU 12. The pressure transducers 14 and 16 are each of a type generally well known in the art and commercially available from a variety of known vendors.

Preferably, apparatus 10 is also combined with a conventional diving computer 24 like those described in U.S. Pat. No. 4,005,282 to Jennings; U.S. Pat. No. 4,192,001 to Villa; and U.S. Pat. No. 4,054,783 to Seireg et al. and/or in U.S. Pat. No. 4,782,338 to Barshinger, all of which are hereby incorporated by reference herein in their entirety. Decompression is discussed in numerous references, including Peter B. Bennett, et al., The Physiology and Medicine of Diving and Compressed Air Work, Williams & Wilkens Company, 1969, also incorporated by reference herein.

The apparatus 10 of the preferred embodiment of the present invention and a diving computer 24 may be combined by the provision of separate packages or elements, as is depicted in FIG. 1 or by the combination of the functions of the subject invention and a conventional diving computer within a single package employing a single CPU or microprocessor (not shown). The diving computer 24 and the associated communication link 25 are indicated in phantom to emphasize that the apparatus 10 of the present invention need not include a diving computer 24 and to further emphasize that in a preferred form, the invention employs a single microprocessor based CPU 12.

One of ordinary skill in this art will also appreciate that CPU 12 would preferably comprise a microprocessor or other processing module together with a memory means or memory 18 of one or more volatile and non-volatile memory modules (RAM, ROM, EPROM, etc.), a clock, a power supply, and other hardware elements, or components typically employed in a microprocessor based computer/control system, all interconnected in a manner known in the art to form a portable, battery-powered hardware system. In addition to an actual display device such as a liquid crystal display, LED display or a plurality of separate devices, the display 20 may further require some form of memory or buffer (e.g., registers, RAM, etc.) and appropriate display drivers to store the data being updated by the CPU 12 and to drive the display 20. All of these components and their functions are well known to those skilled in the art and are commercially available from a variety of sources. It will be appreciated that the present invention is not limited to any particular type of hardware components for the CPU 12, memory 18 or the display 20 and that the type of hardware components employed with differing embodiments of the present invention may vary, depending upon the particular configuration.

The non-volatile portion of the memory 18 is employed for storing one or more programs that contain a series of instructions for performance by the CPU 12. The CPU 12 receives the instructions from the memory 18 in a predetermined sequence and, through interaction with transducers 14 and 16 and the memory 18, performs data manipulation and mathematical calculations to obtain the desired result, namely, a determination of Consumption Rate and Projected Consumption Time at the current ambient pressure and at other ambient pressures. The determined information is then sent by the CPU 12 to the display 20 for display to the user.

Set forth below are several methods of operating the apparatus 10 to provide and display the desired information to the user. It should be understood that while the following discussion and examples illustrate the essential features of this invention, the examples may be varied without departing from the essential features of this invention. Generally, the methods set forth below are implemented within the software installed within the memory 18. As used herein, the terms, "program," "computer program," "software," and "software program," may be interchangeably used to mean a series or sequence of predetermined computer instructions which are used to control the operation of the central processing unit and/or its associated hardware components.

In order to obtain the desired degree of accuracy for the following calculations, the signal value from the both pressure transducers 14 and 16 must be linear and correspond to absolute pressure values (i.e., the signal would equal a value of zero at an absolute pressure of zero). If the electrical characteristics of the transducer reading circuit are otherwise, then the CPU 12 must be programmed to correct the signal values so that they are linear and in direct proportion to the absolute pressure on the respective transducers. In the following discussion, it is assumed that all pressure transducer signals correspond linearly to absolute pressure.

In a relatively simple embodiment, the CPU 12 employs a standard sampling routine to periodically receive a series of gas pressure measurement signals from the high pressure transducer 14. Each of the gas pressure signals represents the instantaneous pressure of the breathable gas within the fixed volume container 22 at each of the sample times. The time interval between sampling the gas pressure signals selected for this embodiment is 15 seconds, although shorter or longer time intervals may alternatively be employed. The CPU 12 thus receives a container gas pressure signal every 15 seconds and temporarily stores each of the signals in a series of predetermined, identifiable, recallable locations within the memory 18.

As discussed above, in order to make a useful (accurate) determination of the Consumption Rate of the breathable gas within the fixed volume container 22, it is necessary to obtain an average Consumption Rate over a relatively long time period to avoid the effects of atypical air usage and other short-term variations. In the present embodiment, the averaging time interval selected is substantially greater than the 15-second intervals employed in sampling and storing the gas pressure signals and, preferably, is a 3-minute time interval. To determine the 3-minute average gas pressure change or drop, it is necessary for the CPU 12 to store in the memory 18 the most recent twelve gas pressure readings taken at the 15-second intervals. As each new gas pressure reading is received, the CPU 12 recalls and removes from memory 18 the oldest stored gas pressure signal (taken three minutes before) and compares the oldest stored pressure signal with the latest gas pressure signal to determine the drop in pressure that occurred in the 3 minute interval between the two measurements. The pressure drop is divided by three to provide the average pressure drop per minute or Consumption Rate. This Consumption Rate is recalculated in this same manner every 15 seconds with each new sampling of the gas pressure within the fixed volume container 22. Thus, a running 3 minute average Consumption Rate is updated every 15 seconds. The CPU 12 then divides the latest reading of stored gas pressure by the average Consumption Rate and makes a determination of Projected Consumption Time. As with the calculation of Consumption Rate, this Projected Consumption Time can be updated every 15 seconds with each new high pressure transducer reading.

It will be appreciated that the Projected Consumption Time generated as described above will be valid only for the particular ambient pressure at which the Consumption Rate was determined. Should the user change his ambient pressure, his pressure Consumption Rate will change according to Boyle's law and the Projected Consumption Time will no longer be valid. It is therefore an essential element of this invention that the determined Consumption Rate be normalized for the ambient pressure at which it was determined. The CPU 12 normalizes the Consumption Rate by dividing the previously obtained Consumption Rate by the signal value received from the ambient pressure transducer 16 at the time that the Consumption Rate is determined. The resulting Normalized Consumption Rate is then used as the basis for determining the Projected Consumption Rate at any ambient pressure. The CPU 12 determines the Projected Consumption Rate at any ambient pressure Pa by multiplying the Normalized Consumption Rate by a valve equivalent to the signal which would be received from the low pressure transducer at ambient pressure Pa, i.e., the signal which would be generated by the low pressure transducer if the low pressure transducer were at the depth corresponding to the particular ambient pressure of interest. The resulting product is the Projected Consumption Rate at the particular ambient pressure or depth Pa.

To find the Projected Consumption Time, the CPU 12 divides the latest reading of the high pressure transducer 14 by the just determined Projected Consumption Rate. In this example, the signal from the low pressure transducer 16 is sampled every 3 seconds. At each sampling, a new calculation is made of Projected Consumption Rate and Projected Consumption Time. Thus the user has the advantage of both a Consumption Rate based on a long term moving average and a Projected Consumption Time updated every 3 seconds.

In the embodiment described here, the Consumption Rate was normalized and then multiplied by a new ambient pressure to determine a Projected Consumption Rate. As will be obvious to one skilled in the art, it is not necessary to actually calculate a Projected Consumption Rate. The Projected Consumption Time (PCT) can be found directly from the Normalized Consumption Rate (NCR) by the formula:

$$PCT = (Pt)/NCR(Pa)$$

Where:
Pa = the signal from the low pressure transducer, and
Pt = the signal from the high pressure transducer.

The foregoing embodiment, while substantially more accurate and responsive than the prior art, can be improved further by refining the method used to determine Consumption Rate. As will be appreciated by those skilled in the art, the Consumption Rate determination described above does not make any correction in the determined Consumption Rate for any changes in depth (ambient pressure) that may have occurred during the three minute averaging period. In the operational method of the second preferred embodiment, greater accuracy is obtained by normalizing the drop between each adjacent gas pressure signal received from the high pressure transducer 14 for the average ambient pressure extant over the 15-second time interval elapsed since the previous reading of the high pressure transducer.

In order to implement the operational method of the preferred embodiment, the CPU 12 samples the signal from the high pressure transducer 14 (Pt) and stores each sampled signal in a register of the memory 18. Simultaneously, the CPU 12 begins sampling the signal from the low pressure transducer (Pa) every 3 seconds. The value of each sampled low pressure transducer signal is additively stored in a second register of the memory 18 until the fifth such signal is received indicating an elapsed time of 15 seconds. Simultaneously with each fifth sampling of the low pressure transducer, the CPU 12 samples the high pressure transducer and, by subtracting the latest reading from the preceding reading of the high pressure transducer, determines the pressure drop that occurred in the preceding 15 second interval. The CPU then normalizes the determined pressure drop by dividing it by the sum of the five signals from the low pressure transducer. The process then begins again after first clearing the Low Pressure storage register and storing the value of the normalized pressure drop in a third register of the memory 18. The third register of memory 18 retains the latest eleven normalized pressure drop values (corresponding to the preceding three minutes). As each new normalized pressure drop determination is made, the eleven most recent previous normalized pressure drops are recalled from the memory 18 and are added to the new normalized pressure drop determination. The resulting sum is then divided by 0.6 to provide a normalized gas Consumption Rate per minute and to serve as the basis for determining the Projected Consumption Time as explained above in connection with the first embodiment (0.6 is used because the 5 Pa readings were not averaged).

Mathematically, the action of this determination can be expressed as follows:

$$NCR = \left(\frac{10}{6}\right) \sum_{i=0}^{i=11} \frac{Pt_{15i} - Pt_{15(i+1)}}{Pa_{15i} + Pa_{15i+3} + Pa_{15i+6} + Pa_{15i+9} + Pa_{15i+12}}$$

Where $\Sigma$ is the sum of 12 iterations (i=0 through 11), each iteration comprising 15 seconds of time; Pt is the pressure signal from the high pressure transducer; and Pa the signal from the low pressure transducer.

Calculation of Projected Consumption Time for any desired ambient pressure is then made as described above in connection with the first embodiment.

In the present preferred method of operation of the apparatus 10, the Consumption Rate is normalized prior to the computation of any Projected Consumption Times. It is equally effective to calculate the Consumption Time for each 15 second change in the gas pressure of the fixed volume container 22 and then normalize and store that result for subsequent averaging and computation of the Projected Consumption Times. It will also be appreciated by those skilled in the art that while the present embodiment employs simple averaging over a three minute time interval in order to smooth out short-term variations in gas usage, it is equally effective to use other types of smoothing techniques, such as weighted averages, as long as the normalization for changes in ambient pressure is made before the averaging occurs.

This embodiment lends itself easily to other methods of determining an average normalized Consumption Rate. For example, the following formula could be used in lieu of the method described above:

$$\overline{NCR_n} = \frac{[\alpha \overline{NCR_{(n-1)}} + NCR_n]}{(\alpha + 1)}$$

Where:
$\overline{NCR}$ is the new Normalized average Consumption Rate,
alpha ($\alpha$) is a scaling constant,
$\overline{NCR_{(n-1)}}$ is the previously determined $\overline{NCR}$, and
$NCR_n$ is the Normalized Consumption Rate for the most recent interval.

This particular averaging method provides a continuous average where, with each new computation, the old NCR values have a diminishing effect on the average. This method determines the NCR of the most recently measured interval and then adjusts the previously determined average NCR to take into account the newly determined NCR. The degree to which the new NCR affects the average NCR is determined by the scaling factor "alpha" ($\alpha$). Increasing the value of $\alpha$ decreases the effect of each new NCR on the new average NCR. Where the NCR determination interval is 15 seconds, a value of about 4 for $\alpha$ results in a useful averaging period for SCUBA instruments. It is important to note that this particular style of averaging is continuous and doesn't really have a defined time limit. What is important to this invention is that the determination of ambient pressure and resulting computation of Consumption time be performed at least five times within the time period where an individual NCR data value makes a measureable difference in the average NCR.

Other averaging methods may be used to find the average NCR including systems that ignore NCR values that deviate substantially from the previously computed average NCR.

A third preferred method of operation of the apparatus 10 of the present invention utilizes changes in the mass of the gas within the fixed volume container 22 for determining Projected Consumption Time. The fixed volume container 22, as with most SCUBA tanks, is labeled to show the actual volume of the gas that the container will hold at a certain pressure. The known volume is generally expressed in units of volume (such as cubic feet) at a particular pressure. Once the volume at a particular pressure is known, it is an easy calculation to convert to units of mass.

In the present embodiment, the volume of the fixed volume container 22 is supplied to the apparatus 10 by the user in any conventional manner such as keypad entry device. The CPU 12 then determines the mass of the available gas within the fixed volume container 22 by multiplying the instantaneous pressure signal obtained from the high pressure transducer 14 by the volume of the container.

The CPU 12 then determines a mass Consumption Rate utilizing changes made in the instantaneous pressure readings from the high pressure transducer 14 over a predetermined time interval, as described above. Alternatively, a differential pressure cell or transducer (not shown) is employed to measure the drop in pressure across an impedance across the line supplying gas to the user. The signal from the differential pressure cell is calibrated to produce an output signal in mass units. The calibrated output signal of the differential pressure cell is integrated into segments defined by the time interval between ambient pressure readings received from the low pressure transducer 16. In the presently preferred embodiment, ambient pressure readings are obtained every two seconds so that the differential pressure cell signal is integrated into 2-second segments. Each segment is then normalized by the CPU 12 by dividing its integrated value by the sum of the ambient pressure readings at the beginning and end of the particular segment. The resulting quotient is the normalized Consumption Rate per second expressed in units of mass and each quotient is stored in a predetermined, recallable memory location. Every two seconds, the CPU 12 recalls the most recent three minutes of the normalized Consumption Rate per second quotients and computes an average to produce a three minute smoothing of the normalized mass Consumption Rate. Once the averaged, normalized Consumption Rate has been determined, a normalized Consumption Time is computed by dividing the mass of the remaining gas available in the fixed volume container 22 by the normalized mass Consumption Rate. Similarly, Projected Consumption Time may be determined for any other ambient pressure by dividing the normalized Consumption Time by that particular ambient pressure.

Regardless of the exact method used to determine the Projected Consumption Time, the information may be displayed to the user in several forms. The simplest form is the display of a single number or value representing the Projected Consumption Time at the present ambient pressure. As the ambient pressure on the user changes, the displayed value will be updated as often as the device reads the low pressure transducer—every 2 or 3 seconds in the embodiments described above.

Figure 2:
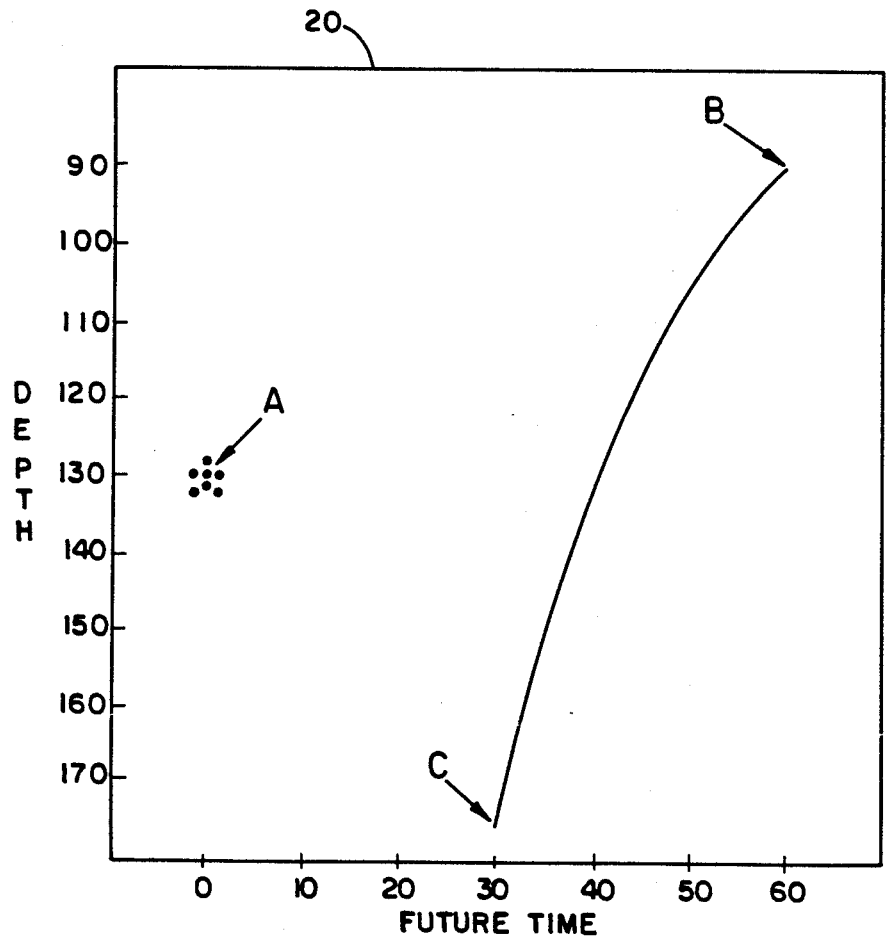
FIG. 2 is a schematic representation of a graphic display employed in a preferred embodiment of the present invention.

The preferred display, however, provides the user with a graphical representation of a range of Projected Consumption Times for many different ambient pressures. FIG. 2 shows a preferred display wherein the user (a SCUBA diver) is represented by the icon labelled "A." Depth is shown on the vertical scale of the display and future time on the horizontal scale. The line "B-C" represents the Projected Consumption Time at the various depths indicated along the left edge of the display. The Projected Consumption Time line is determined by the formula:

$$PCT = (Pt)/NCR(Pa)$$

A significant advantage of the present invention becomes clear from this display, for the diver may quickly see how long his air supply will last at a variety of depths.

For divers, safety considerations will often dictate that the diver return to the surface with a safety margin of air remaining in his SCUBA tank. This requirement is easily accomplished by adding a bias to the high pressure transducer readings or appropriately programming the CPU.

It will be appreciated by those skilled in the art that the above-discussed calculations employed for normalization can alternatively be applied at other points in the process. For example, instead of storing in the memory a series of gas pressure signals or normalized gas pressure readings, the apparatus could store normalized Consumption Rate calculations at a plurality of gas pressures and could maintain a running, weighted average of normalized Consumption Rate. Similarly, the addition step of determining or calculating a normalized Consumption Time could be made prior to the averaging calculation.

It will be recognized by those skilled in the art that the foregoing variations, as well as other changes or modifications, could be made to any or all of the above-described embodiments without departing from the broad inventive concepts of the present invention. Therefore, it should be understood that this invention is not limited to the particular embodiments described above, but it is intended to extend to the entire scope and spirit of the invention as set forth in the appended claims.

I claim:

1. A portable, battery-powered apparatus for determining and displaying the amount of time that a fixed supply of pressurized breathable gas can sustain a consumer who wishes to breath the gas at one or more ambient pressures comprising:

means for measuring the ambient pressure in the vicinity of the consumer at least once every 10 seconds and for generating signals representative of the ambient pressure;

means for measuring the pressure of the supply gas and for generating signals representative of the supply gas pressure;

means for periodically receiving a series of supply gas pressure measurement signals and for periodically determining, from the series of supply gas pressure measurement signals, the average rate at which the supply gas was consumed (Consumption Rate)

over a time at least five times as long as the average time between the ambient pressure measurements;

means for determining a Normalized Consumption Rate by normalizing each determined Consumption Rate to compensate for the ambient pressure on the consumer during the time period over which the Consumption Rate was determined;

means for determining a Normalized Consumption Time by dividing a supply gas pressure measurement by the Normalized Consumption Rate;

means for determining a Projected Consumption Time for one or more ambient pressures of interest by adjusting the Normalized Consumption Time to each ambient pressure of interest; and means for receiving and displaying one or more Projected Consumption Times and one or more associated ambient pressures.

2. A portable, battery-powered apparatus for determining and displaying the amount of time that a fixed supply of pressurized breathable gas can sustain a consumer who wishes to breath the gas at one or more ambient pressures comprising:

means for measuring the ambient pressure in the vicinity of the consumer at least once every 10 seconds and for generating signals representative of the ambient pressure;

means for measuring the pressure of the supply gas and for generating signals representative of the supply gas pressure;

means for receiving the supply gas pressure measurement signals and for determining a change in supply gas pressure over an interval of time;

means for receiving the ambient pressure measurement signals and for normalizing each supply gas pressure change to compensate for the ambient pressure on the consumer during the time when the supply gas pressure change occurred;

means for receiving one or more of said normalized supply gas pressure change determinations and for periodically determining an average normalized rate at which the supply gas was consumed (Normalized Consumption Rate) over a time interval at least five times as long as the time between the ambient pressure measurements;

means for determining a Normalized Consumption Time by dividing a supply gas pressure measurement by the Normalized Consumption Rate;

means for determining a Projected Consumption Time for one or more ambient pressures of interest of periodically adjusting the Normalized Consumption Time to each ambient pressure of interest, said periodic adjustment being made at least five times during the time interval used to determine Consumption Rate; and means for receiving and displaying one or more Projected Consumption Times and one or more associated ambient pressures.

3. A portable, battery-powered apparatus for determining and displaying the amount of time that a fixed supply of pressurized breathable gas can sustain a consumer breathing the gas at one or more ambient pressures comprising:

means for measuring the ambient pressure in the vicinity of the consumer at least once every 10 seconds and for generating signals representative of the ambient pressure;

means for measuring the pressure of the supply gas and for generating signals representative of the supply gas pressure;

means for receiving a series of two or more supply gas pressure measurement signals and for periodically determining, from the series of supply gas pressure measurement signals, the average rate at which the supply gas was consumed (Consumption Rate) over a time interval at least five times as long as the average time interval between the ambient pressure measurements;

means for determining a Projected Consumption Time at the ambient pressure of the most recent ambient pressure measurement based on the determined Consumption Rate and the measured pressure of the supply gas;

means for determining a Projected Consumption Time at one or more additional ambient pressures of interest other than the ambient pressure of the most recent ambient pressure measurement by normalizing at least one of the supply gas pressure measurements, the determined Consumption Rate and the determined Projected Consumption Time at the most recent measured ambient pressure and subsequently converting the normalized result to a Projected Consumption Time at the one or more additional ambient pressures of interest; and means for receiving and displaying one or more Projected Consumption Times and the ambient pressures associated therewith.

4. A portable, battery-powered apparatus for determining and displaying the amount of time that a fixed supply of pressurized breathable gas can sustain a consumer breathing the gas at one or more ambient pressures comprising:

means for measuring the ambient pressure in the vicinity of the consumer at least once every 10 seconds and for generating signals representative of the ambient pressure;

means for measuring the pressure of the supply gas and for generating signals representative of the supply gas pressure;

means for receiving a series of two or more supply gas pressure measurement signals and for periodically determining, from the series of supply gas pressure measurement signals, the average rate at which the supply gas was consumed (Consumption Rate) over a time interval at least five times as long as the average time interval between the ambient pressure measurements;

means for determining a Projected Consumption Time at the ambient pressure of the most recent ambient pressure measurement based on the determined Consumption Rate and the measured pressure of the supply gas;

means for determining a Projected Consumption Time at one or more additional ambient pressure of interest other than the ambient pressure of the most recent ambient pressure measurement by normalizing at least one of the supply gas pressure measurements, the determined Consumption Rate and the determined Projected Consumption Time at the most recent measured ambient pressure and subsequently converting the normalized result to a Projected Consumption Time at the one or more additional ambient pressures of interest; and means for receiving and displaying one or more Projected Consumption Times and the ambient pressures associated therewith.

5. A portable, battery-powered apparatus for determining and displaying the amount of time that a fixed supply of pressurized breathable gas can sustain a consumer breathing the gas at one or more ambient pressures comprising:
- means for measuring the ambient pressure in the vicinity of the consumer at least once every 10 seconds and for generating signals representative of the ambient pressure;
- means for measuring the pressure of the supply gas and for generating signals representative of the supply gas pressure;
- means for receiving a series of two or more supply gas pressure measurement signals and for periodically determining, from the series of supply gas pressure measurement signals, the average rate at which the supply gas was consumed (Consumption Rate) over a time interval of at least one minute;
- means for determining a Projected Consumption Time at the ambient pressure of the most recent ambient pressure measurement based on the determined Consumption Rate and the most recently measured pressure of the supply gas;
- means for determining a Projected Consumption Time at one or more additional ambient pressures of interest other than the ambient pressure of the most recent ambient pressure measurement by normalizing at least one of the supply gas pressure measurements, the determined Consumption Rate and the determined Projected Consumption Time at the most recent measured ambient pressure and subsequently converting the normalized result to a Projected Consumption time at the one or more additional ambient pressures of interest; and
- means for receiving and displaying one or more Projected Consumption Times and the ambient pressures associated therewith.

* * * * *